(12) United States Patent
Donno et al.

(10) Patent No.: US 8,529,631 B2
(45) Date of Patent: Sep. 10, 2013

(54) BASE COMPONENT FOR A TIBIAL IMPLANT

(75) Inventors: Cosimo Donno, Pfungen (CH); Roger Scherrer, Schallhauser (CH)

(73) Assignee: Zimmer, GmbH, Winterthur (CH)

( * ) Notice: Subject to any disclaimer, the term of this patent is extended or adjusted under 35 U.S.C. 154(b) by 565 days.

(21) Appl. No.: 12/175,775

(22) Filed: Jul. 18, 2008

(65) Prior Publication Data

US 2010/0016980 A1    Jan. 21, 2010

(51) Int. Cl.
A61F 2/38    (2006.01)

(52) U.S. Cl.
USPC .................. 623/20.15; 623/20.14; 623/20.18; 623/20.19; 623/20.2; 623/20.32

(58) Field of Classification Search
USPC .................................. 623/20.15, 20.32, 20.33
See application file for complete search history.

(56) References Cited

U.S. PATENT DOCUMENTS

| | | | | |
|---|---|---|---|---|
| 4,207,627 A * | 6/1980 | Cloutier | ..................... | 623/20.21 |
| 4,217,666 A | 8/1980 | Averill | | |
| 5,871,543 A * | 2/1999 | Hofmann | ................... | 623/20.32 |
| RE37,277 E * | 7/2001 | Baldwin et al. | ............ | 623/20.32 |
| 7,066,963 B2 | 6/2006 | Naegerl | | |
| 7,320,709 B2 * | 1/2008 | Felt et al. | ................... | 623/20.16 |
| 7,326,252 B2 | 2/2008 | Otto et al. | | |
| 2003/0139817 A1 * | 7/2003 | Tuke et al. | ................. | 623/20.32 |
| 2005/0055102 A1 | 3/2005 | Tornier et al. | | |
| 2006/0004460 A1 | 1/2006 | Engh et al. | | |

FOREIGN PATENT DOCUMENTS

| | | |
|---|---|---|
| DE | 202004003133 U1 | 7/2004 |
| EP | 0306744 A2 | 3/1989 |
| EP | 0636352 A2 | 2/1995 |
| EP | 0925767 A2 | 6/1999 |
| EP | 1329205 A1 | 7/2003 |
| EP | 1477143 A1 | 11/2004 |
| EP | 1568336 A1 | 8/2005 |
| EP | 2306935 A1 | 4/2011 |
| WO | WO98/58603 A1 | 12/1998 |

OTHER PUBLICATIONS

The Written Opinion and International Search Report mailed Sep. 1, 2009 in related International Application No. PCT/EP2009/004399.
The International Preliminary Report on Patenability mailed Sep. 16, 2010 in the related International Application No. PCT/EP2009/004399.
The Article 34 Amendments to the claims made May 18, 2010, in related International application No. PCT/EP2009/004399.
European Application Serial No. 09776767.7, Office Action mailed Jun. 7, 2011, 3 pgs.
European Application Serial No. 09776767.7, Response filed Aug. 4, 2011 to First Office Action mailed Jun. 7, 2011, 5 pgs.

* cited by examiner

Primary Examiner — David Isabella
Assistant Examiner — Jacqueline Woznicki
(74) Attorney, Agent, or Firm — Schwegman, Lundberg & Woessner P.A.

(57) ABSTRACT

The invention relates to a base component for a tibial implant, comprising a lateral compartment (14), a medial compartment (12) and an anterior connection portion (16) which connects the lateral compartment (14) and the medial compartment (12) to one another at anterior. A portion (18) open to posterior is provided between the lateral compartment (14) and the medial compartment (12). The lateral component (14) and the medial component (12) each have a lower side and an upper side, with at least one of the lower sides being configured for the fastening of the base component to the tibia. A marginal web (22, 22') is formed at at least one of the compartments (12, 14), starting from the upper side, said marginal web forming a receiving shell for a meniscus component (30, 32) of the tibial implant together with the upper side of the compartment. The height of the marginal web (22, 22') in a posterior region is reduced with respect to other regions of the marginal web (22, 22') at at least one of the two compartments (12, 14). The invention furthermore relates to a tibial implant and to a knee prosthesis.

18 Claims, 5 Drawing Sheets

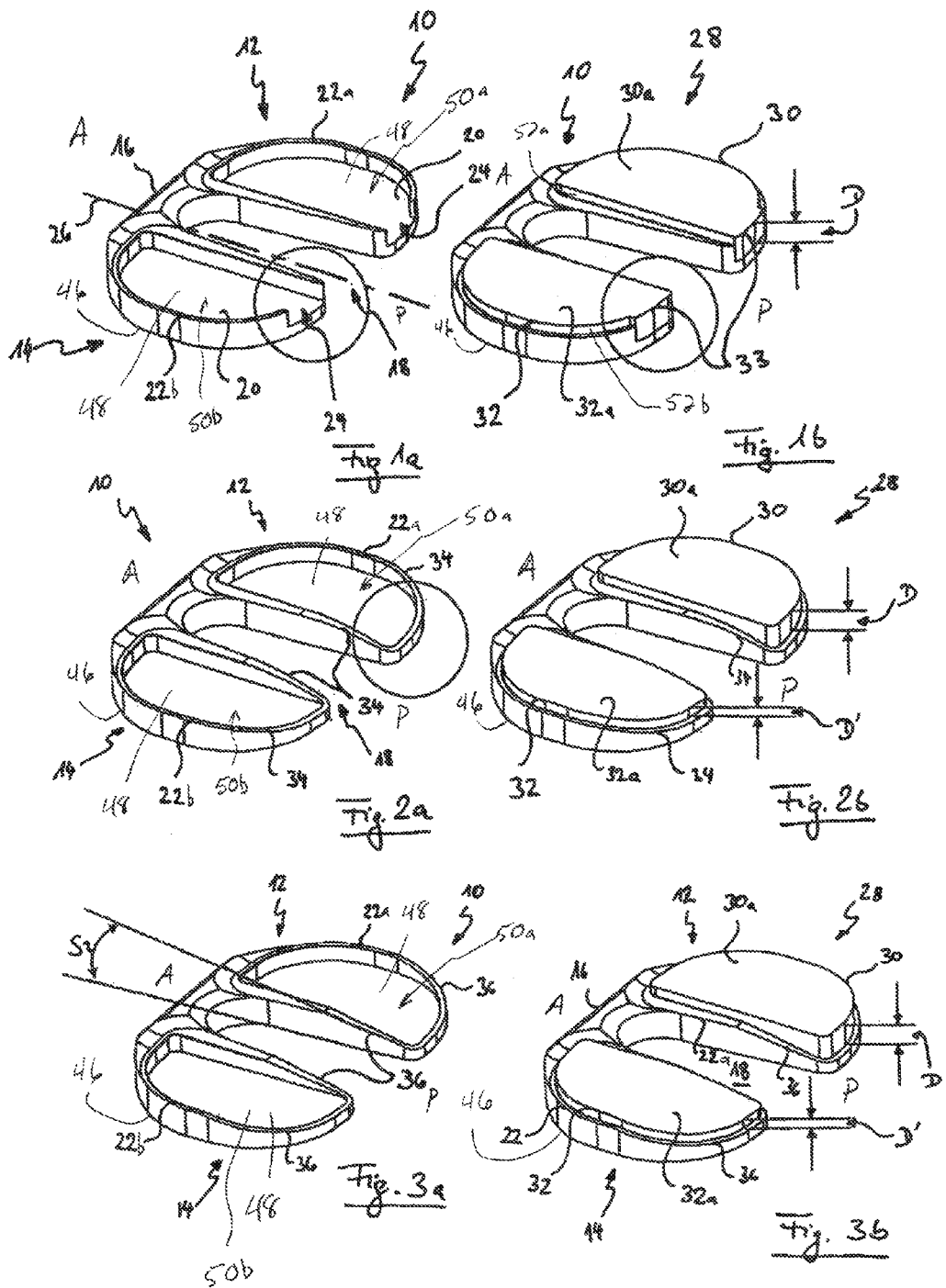

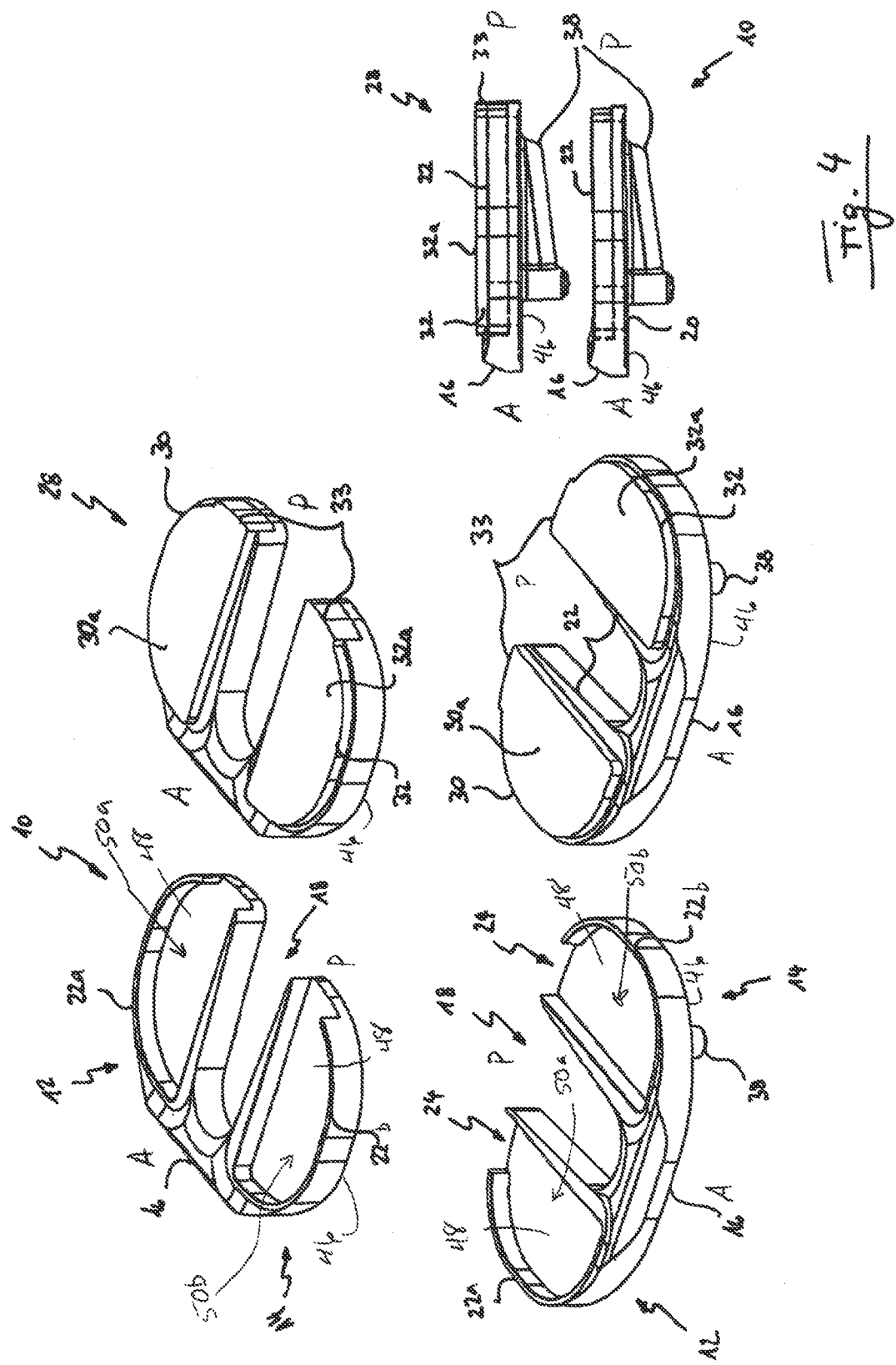

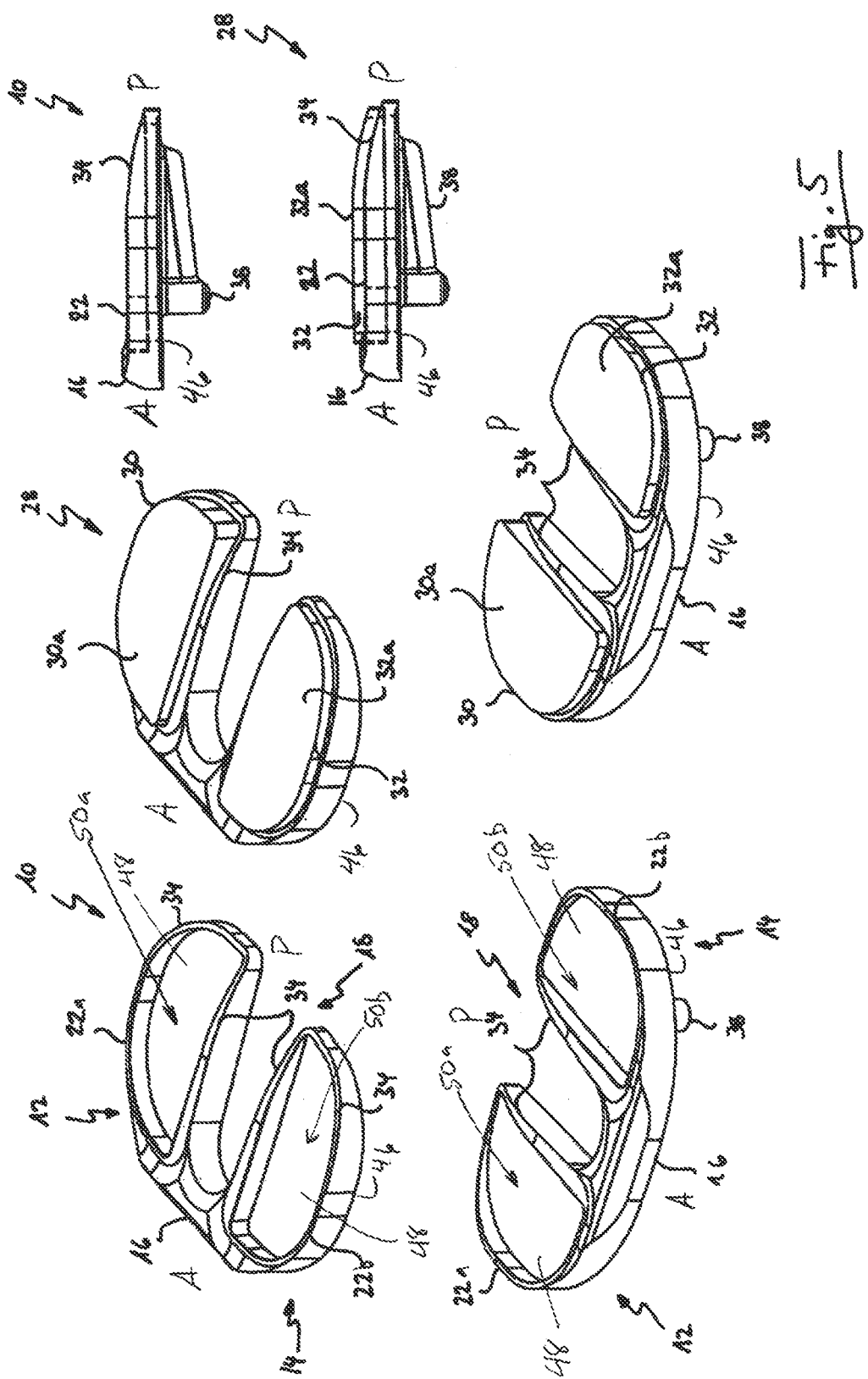

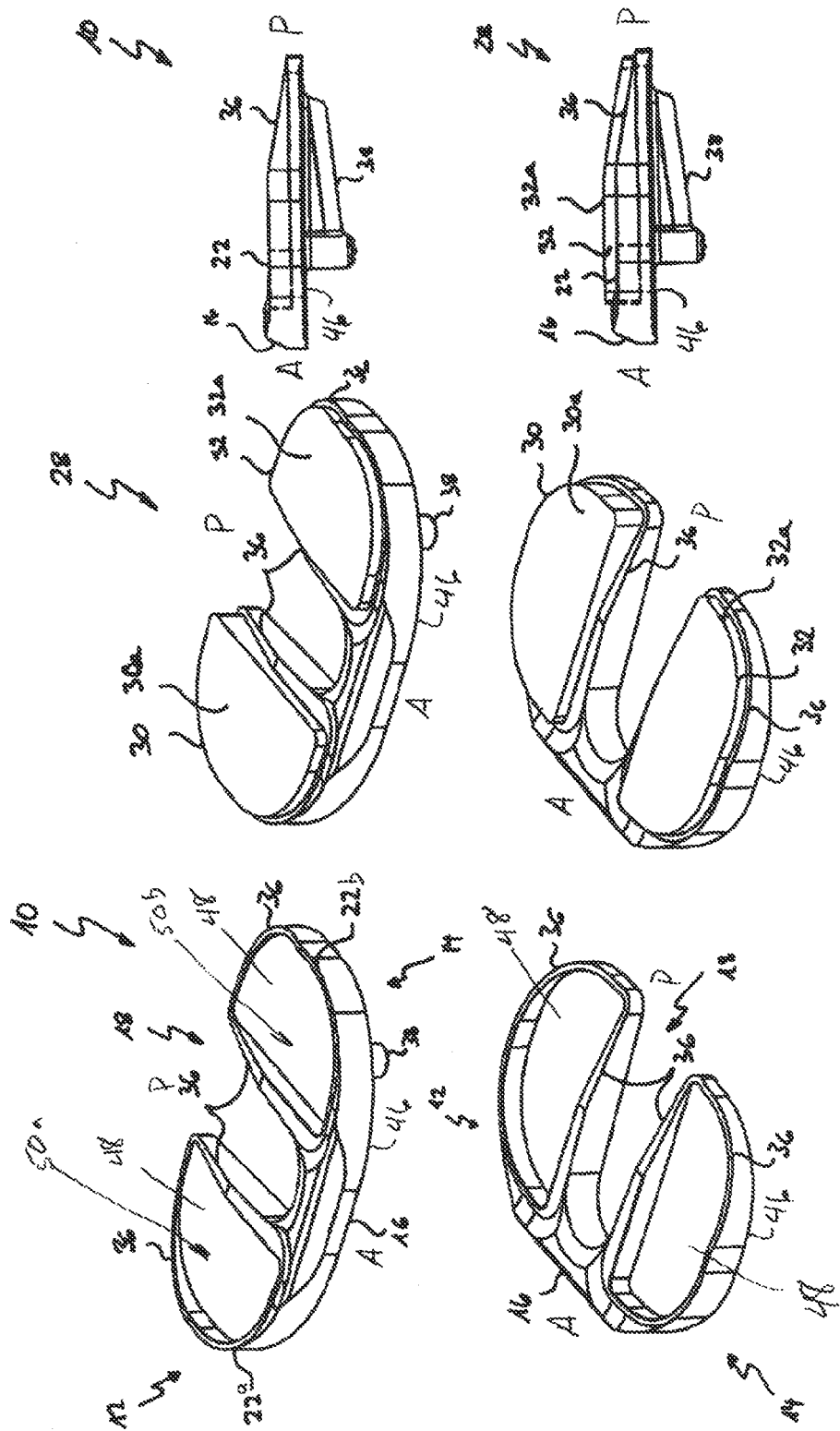

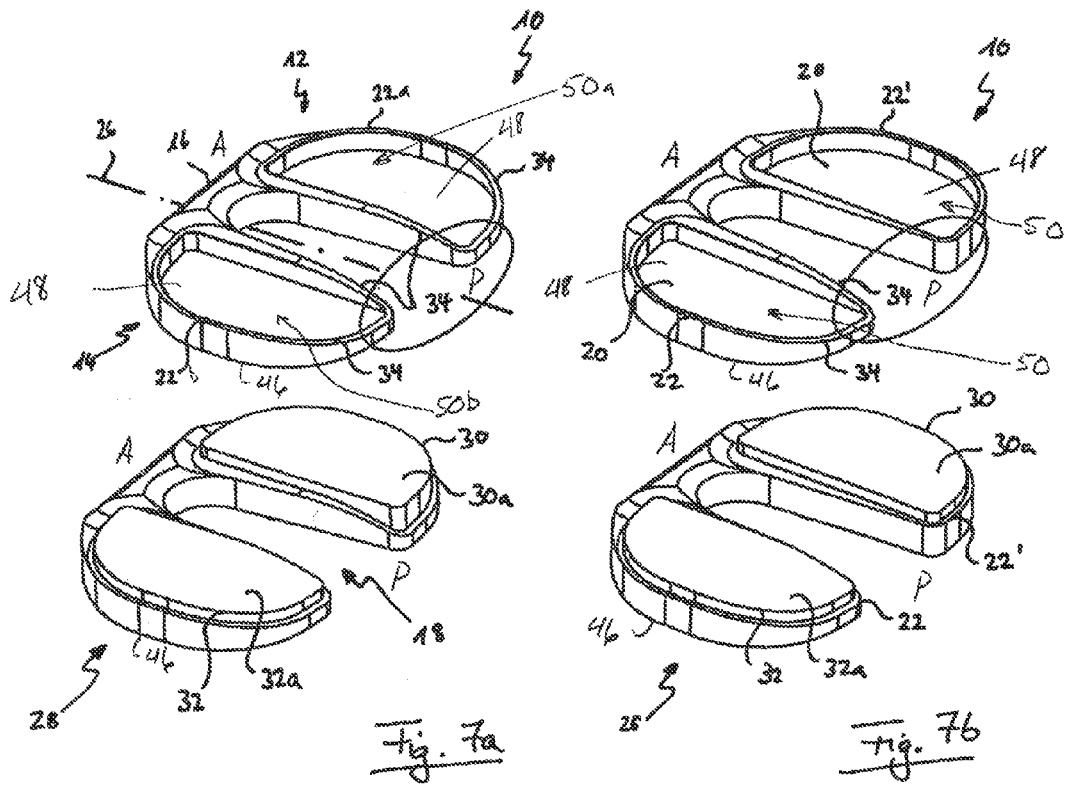
Fig. 7a Fig. 7b
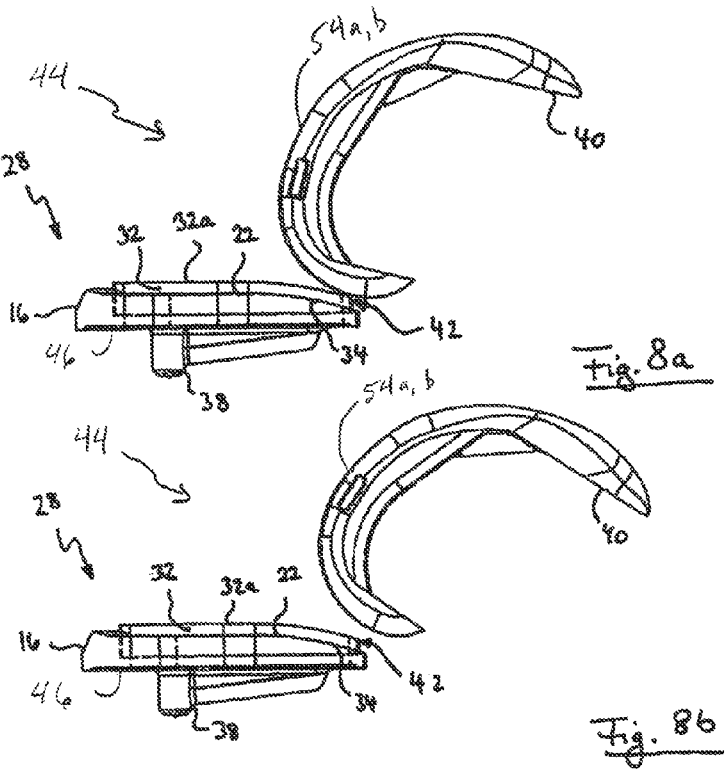
Fig. 8a
Fig. 8b

BASE COMPONENT FOR A TIBIAL IMPLANT

BACKGROUND

Field of the Invention

The invention relates to a base component for a tibial implant of a knee joint prosthesis. The invention furthermore relates to a corresponding tibial implant and to a corresponding knee prosthesis.

The use of knee prostheses can be necessary when the knee joint of a patient is damaged and therefore causes pain and/or is restricted in its functional capability. Such a knee prosthesis usually includes a femoral implant as well as a tibial implant. Bone resurfacing, including implant resurfacing, may also be employed. The function of a healthy knee joint should be simulated as faithfully to nature as possible by the implants, on the one hand. On the other hand, the implants should be designed such that wear is minimized or such that changes to the implants due to wear lead to effects on the function of the knee joint prosthesis which are as small as possible. Moreover, the tibial implant should have a thickness which is as low as possible to minimize the bone resection required for the preparation of the implanting of the prosthesis.

SUMMARY

The invention satisfies these and other demands. The base component set forth here for a tibial implant includes a lateral compartment, a medial compartment and an anterior connection portion which connects the lateral compartment and the medial compartment to one another at anterior. A section open to posterior is provided between the lateral compartment and the medial compartment. The lateral component and the medial component each have a lower side and an upper side, with at least one of the lower sides being configured for the fastening of the base component to the tibia. A marginal web is formed at at least one of the compartments, starting from the upper side, said marginal web forming a receiving shell for a meniscus component of the tibial implant together with the upper side of the compartment. Furthermore, the height of the marginal web at a posterior region is reduced with respect to other regions of the marginal web at at least one of the two compartments.

In other words, the base component set forth here serves as a foundation for the meniscus components of the tibial implant anchored to the tibia. A respective compartment is provided at the base component for the fastening of the meniscus components. The compartments are connected to one another in an anterior region by a connection web. The compartments furthermore each form a receiving shell for the respective meniscus component, with the receiving shell being bounded at the margin by the marginal web. However, the marginal web is not equally high peripherally, but is lowered at at least one compartment in a posterior region, with the term "posterior region" not only including a posterior edge of the base component, but also relating to marginal portions, that is medial and lateral portions, of the compartment.

It is generally also possible for both compartments to have a lowered portion, that is a reduction in the height, of the marginal web in a posterior region.

Such a design of the base component takes account of the anatomical conditions and of the kinematics of a knee joint and, inter alia, improves the cooperation of the tibial implant with the femoral implant of a knee joint prosthesis, in particular in an angled state of the knee in which the posterior region of the tibial implant—and thus also the base component—is under particular strain.

An extended service life of the tibial implant is in particular hereby achieved with a given thickness of the meniscus component particularly in the posterior region especially affected by a wear problem due to the lowered portion of the marginal web. In other words, there is more meniscus component material between the upper edge of an original articulation surface, i.e. the side of the meniscus component facing the femoral implant, and the upper edge of the marginal web in the posterior region of the tibial implant—compared with conventional tibial implants—so that a wear state of the meniscus component requiring revision only occurs later—if at all. A wear state requiring revision is in particular present when the spacing between the upper edge of the articulation surface of the meniscus component and the upper edge of the marginal web has become so low that there is a risk that the marginal web and the femoral implant come into direct contact with one another on knee joint movements.

If, however, the tibial implant should be configured as flat as possible—for example to simplify an implanting operation—or if it should be matched even better to the anatomical relationships, it is possible that, in addition to the marginal web, the articulation surface of the meniscus component (or the articulation surfaces of both meniscus components) also have a drop in height/a reduction in thickness in the posterior region, with no compromises in service life having to be accepted—compared with conventional tibial implants—due to the lowered portion of the marginal web.

It is generally possible for the implanting of the base component set forth here or of the tibial implant set forth here to take place in a minimally invasive manner.

In an embodiment, the height of the marginal web is reduced at least approximately to zero in a posterior region so that the marginal web is interrupted in the posterior region.

Provision is made in a further aspect of the base component for the vertical course of the marginal web to include at least one step at a transition to the posterior region. It is furthermore possible for the vertical course of the marginal web to extend constantly at a transition to the posterior region.

The vertical extent of the marginal web in particular includes an inclined portion with a constant gradient in a transition to the posterior region.

In accordance with an aspect of the base component, the vertical course of the marginal web may include a curved extent at a transition to the posterior region. The curved transition may be a compound curvature formed by multiple radii. The curved transition may also be ellipse shaped. The curved extent of the transition in one exemplary embodiment has a constant radius of curvature.

In accordance with an embodiment, the marginal web otherwise, i.e. apart from the posterior region, has a constant height. Provision is optionally made for the marginal web to extend around the compartment in a closed manner at least outside the posterior region.

In a further embodiment of the base component, it is made of metal. In alternative embodiments, the base component is made from a ceramic material.

The invention furthermore relates to a tibial implant which includes a base component in accordance with one of the embodiments described above. The tibial implant furthermore includes a medial and a lateral meniscus component which each have a fastening surface and an articulation surface. The geometry of the fastening surface corresponds to the receiving shell of the respective compartment so that a reliable positioning of the meniscus component in the base component is ensured.

In an aspect of the tibial implant, the lateral and the medial meniscus components have articulation surfaces of different contours. In other words, the topographies of the articulation surfaces of the two meniscus components differ.

In accordance with a further aspect of the tibial implant set forth here, the articulation surface of a first meniscus component includes a convexly contoured region in a sagittal section. The first meniscus component is in particular the lateral meniscus component. Furthermore, the posterior region of the articulation surface is, for example, convexly contoured. At least one part region of the articulation surface thus has a curvature and is not made in a completely planar fashion. A posterior arrangement of the curved region simplifies the rolling off of the corresponding femoral implant of the knee joint prosthesis.

In accordance with a further development of the tibial implant set forth here, the articulation surface of the first meniscus component, in particular of the lateral meniscus component, includes a posterior portion. In the posterior portion, the articulation surface is inclined toward the fastening surface—that is in the direction of the tibia—in the posterior direction.

In a further modification of the tibial implant, the thickness of the first meniscus component decreases constantly to posterior in a posterior portion.

In a further embodiment of the tibial implant set forth here, the articulation surface of a second meniscus component, in particular of the medial meniscus component, is shaped in planar or concave form.

The meniscus components can be made of suitable polymers including polyethylene. Other bearing materials known in the art may also be used.

The invention furthermore relates to a knee prosthesis including a tibial implant in accordance with one of the embodiments described above and a femoral implant, with the femoral implant including a lateral and a medial articulation surface. The articulation surfaces of the femoral implant are configured to cooperate with the corresponding articulation surfaces of the meniscus components of the tibial implant.

All indications of alignment, positioning, orientation and direction which are used as required both in the claims and in the description and in the drawings in connection with the subject matters set forth here and selected in accordance with the technically usual conventions and which in particular relate to anatomical axes, planes, directions in space and directions of movement are familiar to the person skilled in the art and relate to the implanted state.

BRIEF DESCRIPTION OF THE DRAWINGS

The invention will be explained in more detail in the following with reference to embodiments illustrated in the drawing. The embodiments and the drawings should only be understood as being instructive and not serving for the limitation of the subject matters described in the claims. The representations have been simplified in the drawings; details not necessary for the understanding of the invention have been omitted.

There are shown in the drawings:

FIGS. 1a and b: an embodiment of a tibial implant of the kind set forth here with and without meniscus components;

FIGS. 2a and b: a further embodiment of a tibial implant of the kind set forth here with and without meniscus components;

FIGS. 3a and b: a further embodiment of a tibial implant of the kind set forth here with and without meniscus components;

FIG. 4: a combination of different views of the tibial implant of FIGS. 1a and b;

FIG. 5: a combination of different views of the tibial implant of FIGS. 2a and b;

FIG. 6: a combination of different views of the tibial implant of FIGS. 3a and b;

FIG. 7a: a representation of the embodiment of a tibial implant shown in FIGS. 2a and b;

FIG. 7b: an embodiment of a tibial implant of the kind set forth here with differently configured compartments;

FIGS. 8a and 8b: an embodiment of the tibial implant of the kind set forth here in a side view in a joint view with a femoral component.

The embodiments serve for the better understanding of the invention and should not be used for the limitation of the invention set forth in the claims.

DETAILED DESCRIPTION

FIG. 1a shows a base component 10 which comprises a medial compartment 12 and a lateral compartment 14. The two compartments 12, 14 are connected to one another by a connection web 16. The connection web 16 is arranged in an anterior region of the base component 10 and therefore forms an anterior connection portion. A section 18 open to posterior thereby results between the compartments 12, 14. Anterior aspect of the base component A and posterior aspect of the base component P of the prostheses of the present disclosure are marked in FIGS. 1a-7b extending from upper side 48.

It can be recognized from the perspective view of the base component 10 from a lateral-posterior angle of view from above that both the medial component 12 and the lateral component 14 have receiving shells 50 which are each formed by a base plate 20 and a marginal web 22. Marginal web 22 can take the form of medial marginal web 22a or lateral marginal web 22b. Receiving shells 50 may take the form of medial receiving shell 50a or lateral receiving shell 50b. Referring to FIG. 1b, medial meniscus component 30 and lateral meniscus component 32 include medial fastening surface 52a and lateral fastening surface 52b, respectively. The base plate 20 extends substantially parallel to a transverse plane.

In the posterior region, the compartments 12, 14 each have a cut-out 24 in the extent of the respective marginal webs 22 which is emphasized by a circle for illustration in the lateral compartment 14. In the embodiment shown, the cut-outs 24 and marginal webs 22 of the compartments 12, 14 are substantially symmetrical to a longitudinal axis 26 of the base component 10 extending in the anterior-posterior direction. The cut-outs 24 and marginal webs 22 can, however, generally also have different configurations at the compartments 12, 14. Apart from the cut-outs 24, the marginal webs 22 have a constant height relative to the base plates 20.

FIG. 1 shows a tibial implant 28 which comprises the base component 10 described with reference to FIG. 1 and a medial meniscus component 30 and a lateral meniscus component 32.

The two meniscus components 30, 32 each have a projection 33 which is shaped such that it fits into the corresponding cut-out 24 of the respective compartment 30, 32.

The medial meniscus compartment 30 and the lateral meniscus compartment 32 have a constant thickness D, as can be recognized by a comparison of the extent of the upper edge of the meniscus components 30, 32 and of the extent of the marginal webs 22. Since the marginal webs 22—as already stated above—have a constant height relative to the base plate 20 with the exception of the cut-outs 24, this thus also applies to the meniscus components 30, 32 so that an articulation surface 30a of the medial meniscus component 30 and an articulation surface 32a of the lateral meniscus component 32 extend substantially parallel to the plane spanned by the base plates 20.

In this state, the tibial implant 28 shown forms the component of a knee joint prosthesis on the tibial side. Before the base component 10 of the tibial implant 28 is fastened to the tibia (not shown) of a patient, the proximal part of the tibia is surgically prepared. A preparation of this type—or a resection—of the bone provides a resection surface to which at least one of the base plates 20 and thus the base component 10 can be fastened.

Another embodiment of the base component 10 is shown in FIG. 2a. The base components 10 of FIGS. 1a and 2a are similar to large extents. However, the aspect of the posterior region of the components 12, 14 differs. For example, no cut-out 24 is thus provided. Instead, the respective marginal web 22 of the compartments 12, 14 is only lowered and not interrupted in the posterior region. As can be recognized particularly clearly at the side of the medial compartment 12 facing the section 18, the height of the marginal web 22 reduces toward posterior from a region disposed approximately in the center between the anterior end and the posterior end of the medial compartment 12.

In the embodiment shown, the vertical drop of the upper edge of the marginal web 22 is configured as a convex curvature 34 at the sides of the marginal webs 22 facing the section 18. The portions of the marginal web 22 falling to posterior at the outer sides of the compartments 12, 14 also each have a convex curvature 34 as will be explained in the following with reference to FIG. 5.

The extent of the marginal web 22 has no jumps or steps. Furthermore, the extent of the marginal web 22 of the two components 12, 14 is substantially the same, i.e. symmetrical to the longitudinal axis 26 of the base component 10.

FIG. 2b shows a corresponding tibial implant 28 which includes the base component 10 of FIG. 2a. In contrast to the tibial implant 28 shown in FIG. 1b, the medial meniscus component 30 and the lateral meniscus component 32 differ. Whereas the medial meniscus component 30 has a substantially constant thickness D, the posterior thickness D' of the lateral meniscus component 32 is smaller than its thickness in the anterior region. In other words, the articulation surface 32a of the lateral meniscus component 32 falls toward posterior. In the embodiment shown here, the outer edge of the articulation surface 32a extends substantially parallel to the upper edge of the marginal web 22, with these extents also being able to differ from one another, however, depending on the demands and on anatomical conditions. The articulation surface 32a thus has a surface curved in the anterior-posterior direction.

The articulation surface 30a of the medial meniscus component 30 has no drop in the posterior region, but extends substantially parallel to the surface of the base plate 20 or parallel to the plane which is formed by the upper edge of the marginal web 22 in the anterior region of the base component 10.

The different configuration of the meniscus components 30, 32 represents a matching of the implant geometry for the improved simulation of the natural knee kinematics.

FIG. 3a shows a further embodiment of the base component 10. Similar to the variant shown in FIG. 2a, it has an extent of the marginal webs 22 lowered at posterior. However, the portions of the marginal webs 22 of the compartments 12, 14 facing the section 18 do not have any curves, but inclined surfaces 36 with a constant gradient angle S relative to the plane of the base plates 20. The posterior portions of the marginal webs 22 at the outer sides of the compartments 12, 14 likewise fall—observed in a projection in a sagittal plane—with a constant gradient. The gradients 36 merge constantly into a respective posterior portion of the marginal webs 22 at their posterior ends.

FIG. 3b shows the corresponding tibial implant 28 with meniscus components 30, 32, with the medial meniscus component 30 corresponding to the medial meniscus component 30 of FIG. 2b, that is having a constant thickness D. The outer edge of the lateral articulation surface 32a extends—as in FIG. 2b—substantially parallel to the outer edge of the marginal web 22. A different design of the articulation surface 32a thereby results in comparison with FIG. 2b since the marginal webs 22 drop in linear fashion. The articulation surface 32a of FIG. 3b is therefore substantially an inclined surface with a constant gradient angle S in the anterior-posterior direction.

Generally, curved portions and portions falling in linear fashion can also be combined to form the marginal webs 22 in the posterior region of the compartments 12, 14. The articulation surfaces 30a, 32a can also have shapes which differ from those described above and are optionally more complex. Different inclination/curvature components of the articulation surfaces 30a, 32a can thus be provided—also in a combined form. The articulation surfaces 30a, 32a can, for example, also have concave/convex curvatures in the lateral-medial direction.

FIG. 4 shows the embodiment of the base component 10 or of the tibial implant 28 already described with reference to FIGS. 1a and 1b from two additional views (perspective view from obliquely anterior and a lateral view). The additional views illustrate the constant height of the marginal webs 22 of the compartments 12, 14 over their total extent with the exception of the posterior cut-outs 24. Furthermore, it can be seen from the view from obliquely anterior (bottom left, without meniscus components 30, 32) that the portions of the marginal webs 22 have a substantially constant width at the outer sides of the base component 10, whereas the portions facing the section 18 have a width reducing from anterior to posterior.

The side views (FIG. 4, right) show anchorage means 38 extending from lower side 46 of the base plate 20 of the lateral compartment 14 facing the tibia (not shown). They serve for the fastening of the base component 10 to the tibia.

FIG. 5 shows analog to FIG. 4 further views of the base component 10 or of the tibial implant 28 of FIGS. 2a and 2b. It can be seen from the view from obliquely anterior that the marginal webs 22 of the compartments 12, 14 in the posterior region only have a low height, but are not interrupted.

The side views of the base component 10 or of the tibial implant 28 (FIG. 5, right) show the convexly curved character of the articulation surface 32a of the lateral meniscus component 32. The posterior region of the marginal web 22 at the outer side of the lateral compartment 14 likewise has a corresponding curvature 34. Provision can, however, be made that this region of the marginal web 22 has an extent of curvature which differs from the extent of curvature of the articulation surface 32a.

FIG. 6 shows additional views of the base component 10 and of the tibial implant 28 of FIGS. 3a and 3b. In particular the side views (FIG. 6, right) show the thickness of the lateral meniscus component 32 which reduces to posterior, with the fall in the thickness D being limited to the posterior region— in another respect as in the case of the embodiment of FIG. 5—and being made substantially parallel to the extent of the marginal web 22.

FIG. 7a again shows the base component 10 of FIG. 2a. This embodiment, which is substantially symmetrical with respect to the longitudinal axis 26 serves for the comparison with a further embodiment—shown in FIG. 7b—of the base component 10, whose compartments 12, 14 have differently pronounced marginal webs 22, 22'. Whereas the lateral compartment 14 has a marginal web 22 having a vertical profile the same as the marginal web 22 of the compartment 14 shown in FIG. 7a, the height of the marginal web 22' of the medial compartment 12 is constant with respect to the base plate 20. This difference becomes particularly clear by a comparison of the regions characterized by the ovals.

The tibial implants 28 of FIGS. 7a and 7b include medial and lateral meniscus components 30, 32 which differ from one another in order to—as already mentioned—simulate anatomical conditions of a natural knee joint as well as possible at least in a functional respect. The medial meniscus component 30 of the tibial implant 28 of FIG. 7b is the same as that of the tibial implant 28 of FIG. 7a. The same applies to the lateral meniscus component 32.

Deviating from the embodiments shown, the medial meniscus component 30 can likewise have a curvature, with this in particular being of a concave configuration.

The effect of the posterior reduction in the marginal web height will be explained in the following with reference to FIGS. 8a and 8b.

Knee prosthesis 44 is illustrated in FIGS. 8a and 8b. FIG. 8a shows a lateral view of the tibial implant 28 of FIGS. 2a and 2b as well as of FIG. 5. In addition, an exemplary femoral component 40 is shown, with an angled state of a knee joint prosthesis being shown. A rolling off of the femoral component 40 on the articulation surface 32a is particularly improved in a very angled state of the knee by the thickness of the lateral meniscus component 32 which reduces to posterior. The femoral component 40 therefore does not roll off on the angling of the knee—or if does roll off, then only substantially later—via a posterior edge 42 of the lateral meniscus component 32, whereby wear of the meniscus component 32 is reduced, for example. The posterior reduction in the height of the marginal web 22 furthermore reduces the probability that portions of the marginal web 22 come into direct contact with the femoral component 40 on increasing wear of the lateral meniscus component 32.

The condyle design of the present invention facilitates femoral rollback. In certain current designs, edge loading of the bearing component is experienced under high flexion conditions which can results in high pressures on the meniscal component. The sloped design of the present invention results in surfacing loading even under high flexion as illustrated in FIG. 8a or a lift off of the femoral condyle from the meniscal component as illustrated in FIG. 8b.

The aspects of the posterior region of a base component 10 of a tibial implant 28 and of a tibial implant 28 shown here thus result in an improved function of the knee joint prosthesis and increase the latter's service life.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

REFERENCE NUMERAL LIST

10 base component
12 medial compartment
14 lateral compartment
16 connection web
18 section
20 base plate
22, 22' marginal web
24 cut-out
24a projection
26 longitudinal axis
28 tibial implant
30 medial meniscus component
30a articulation surface
32 lateral meniscus component
32a articulation surface
33 projection
34 curvature
36 inclined surface
38 anchorage means
40 femoral component
42 posterior edge
D, D' thickness
S gradient angle
22a medial marginal web
22b lateral marginal web
44 knee prosthesis
46 lower side
48 upper side
50 receiving shell
50a medial receiving shell
50b lateral receiving shell
52a medial fastening surface
52b lateral fastening surface
54a medial articulation surface
54b lateral articulation surface
A anterior aspect of the base component
P posterior aspect of the base component

What is claimed is:

1. A base component for a tibial implant, comprising:
  a lateral compartment;
  a medial compartment;
  an anterior connection portion connecting the lateral compartment and the medial compartment to one another at an anterior region of the base component wherein a section open to a posterior region of the base component is provided between the lateral compartment and the medial compartment, and wherein the lateral compartment and the medial compartment each have a lower side and an upper side, with at least one of the lower sides being configured for the fastening of the base component to the tibia; and
  a marginal web having a marginal web height that defines a receiving shell around at least one of the lateral and medial compartments, the receiving shell configured for receiving a meniscus component of the tibial implant, wherein the marginal web height is reduced in the posterior region of the base component as compared to the anterior region of the base component.

2. The base component of claim 1, wherein the marginal web height is reduced at least approximately to zero in the posterior region such that the marginal web is interrupted in the posterior region.

3. The base component of claim 1, wherein the marginal web height includes at least one step at a transition to the posterior region.

4. The base component of claim 1, wherein the marginal web extends with a constant gradient from the posterior region to a transition.

5. The base component of claim 1, wherein the marginal web includes a declined portion with a constant gradient from a transition to the posterior region.

6. The base component of claim 1, wherein the marginal web height includes a curved extent at a transition to the posterior region.

7. The base component of claim 6, wherein the curved extent of the transition has a constant radius of curvature.

8. The base component of claim 1, wherein the marginal web height is constant in all areas other than the posterior region.

9. The base component of claim 1, wherein the marginal web extends at least partially around at least one of the lateral and medial compartments in a closed manner at least outside the posterior region.

10. The base component of claim 1, wherein the base component is made of metal.

11. The base component of claim 1, wherein the base component is made of a ceramic material.

12. A tibial implant, comprising:
a base component, comprising:
a lateral compartment;
a medial compartment;
an anterior connection portion connecting the lateral compartment and the medial compartment to one another at an anterior region of the base component, wherein a section open to a posterior region of the base component is provided between the lateral compartment and the medial compartment, and wherein the lateral compartment and the medial compartment each have a lower side and an upper side, with at least one of the lower sides being configured for the fastening of the base component to the tibia;
a lateral marginal web having a lateral marginal web height defining the lateral compartment starting from the upper side of the lateral compartment, wherein the lateral marginal web height is reduced in the posterior region of the base component as compared to the anterior region of the base component; and
a medial marginal web having a medial marginal web height defining the medial compartment starting from the upper side of the medial compartment, wherein the marginal height of at least one of the lateral marginal web height and the medial marginal web height is reduced in the posterior region of the base component with respect to the anterior region of the base component;
a medial meniscus component,
and a lateral meniscus component; wherein
the medial marginal web, together with the upper side of the medial compartment, form a medial receiving shell configured for receiving the medial meniscus component, the medial receiving shell being bounded at its margin by the medial marginal web;
the medial meniscus component having a medial fastening surface and a medial articulation surface, with a geometry of the medial fastening surface corresponding to the medial receiving shell of the medial compartment so that a reliable positioning of the medial meniscus component in the base component is ensured; and
wherein the lateral marginal web, together with the upper side of the lateral compartment, form a lateral receiving shell configured for receiving the lateral meniscus component, the lateral receiving shell being bounded at its margin by the lateral marginal web;
the lateral meniscus component having a lateral fastening surface and a lateral articulation surface, with a geometry of the lateral fastening surface corresponding to the lateral receiving shell of the lateral compartment, so that a reliable positioning of the lateral meniscus component and the base component is ensured.

13. The tibial implant of claim 12, wherein the medial articulation surface of the medial meniscus component is shaped in one of a planar and a concave fashion.

14. The tibial implant of claim 12, wherein the medial and lateral meniscus components are each made of plastic.

15. A knee prosthesis comprising the tibial implant of claim 12, and a femoral implant, wherein the femoral implant includes a lateral articulation surface and a medial articulation surface, and wherein the medial articulation surface and the lateral articulation surface of the femoral implant are configured to cooperate with the corresponding articulation surfaces of the medial and lateral meniscus components of the tibial implant.

16. The base component of claim 5, wherein the marginal web height is constant relative to the upper side of the compartment from the anterior region to the transition.

17. The base component of claim 5, wherein the declined portion with the constant gradient is on the marginal web adjacent the section open to the posterior region.

18. The base component of claim 1, wherein the marginal web height on an outside of the lateral or medial compartment decreases from a transition toward the posterior region.

* * * * *